United States Patent
Dodsworth et al.

(10) Patent No.: US 8,371,092 B1
(45) Date of Patent: Feb. 12, 2013

(54) APPARATUS AND METHODS FOR REDUCING CAPSULE ELONGATION

(75) Inventors: David W Dodsworth, Furlong, PA (US); Jack Bradley, Downingtown, PA (US); Jeffery A Rudy, Norwich, NY (US); Todd M Hall, Norwich, NY (US); Paul Barnhart, Maryland, NY (US)

(73) Assignee: Viropharma Incorporated, Exton, PA (US)

( * ) Notice: Subject to any disclaimer, the term of this patent is extended or adjusted under 35 U.S.C. 154(b) by 455 days.

(21) Appl. No.: 12/555,602

(22) Filed: Sep. 8, 2009

Related U.S. Application Data

(60) Provisional application No. 61/094,791, filed on Sep. 5, 2008.

(51) Int. Cl.
*B65B 63/08* (2006.01)

(52) U.S. Cl. ............... 53/127; 53/454; 53/431; 53/432; 53/440

(58) Field of Classification Search ............ 53/454, 53/453, 428, 432, 433, 440, 111 R, 127, 431
See application file for complete search history.

(56) References Cited

U.S. PATENT DOCUMENTS

| | | | | |
|---|---|---|---|---|
| 4,028,024 A | * | 6/1977 | Moreland | 425/133.1 |
| 4,522,666 A | * | 6/1985 | Wittwer | 156/69 |
| 4,584,817 A | * | 4/1986 | Yamamoto et al. | 53/329.2 |
| 4,978,483 A | * | 12/1990 | Redding, Jr. | 264/4.32 |
| 5,054,258 A | * | 10/1991 | Tait et al. | 53/137.2 |
| 5,085,033 A | * | 2/1992 | Graham | 53/436 |
| 5,146,758 A | * | 9/1992 | Herman | 62/62 |
| 5,456,919 A | * | 10/1995 | Patell et al. | 424/451 |
| 5,761,886 A | * | 6/1998 | Parkhideh | 53/454 |
| 5,876,777 A | * | 3/1999 | Zimmermann et al. | 426/420 |
| 5,916,590 A | * | 6/1999 | Cody et al. | 424/452 |
| 7,082,738 B2 | * | 8/2006 | Konishi et al. | 53/281 |
| 2001/0004056 A1 | * | 6/2001 | Sawyer | 206/503 |
| 2008/0000099 A1 | * | 1/2008 | Victorov et al. | 34/129 |

OTHER PUBLICATIONS

Product Brochure entitled: "Dorner 5200 Qwik Series" from http://www.dornerconveyors.com/5200/belting.asp dated before Sep. 5, 2009.
Gennaro et al., Pharmaceutical Necessities, Remington's Pharmacuetical Sciences, 1985, pp. 1278-1320, Chapter 68, Mack Publishing Company, Easton, PA.
Yao et al, Glycopeptides: Classification, Occurrence and Discovery, Glycopeptides Antibiotics, 1994, pp. 1-27, vol. 63, Marcel Dekker Inc., New York, NY.
U.S. Appl. No. 11/789,652, filed Apr. 25, 2007, entitled: Liquid Delivery System.
U.S. Appl. No. 12/369,479 filed Feb. 11, 2009, entitled: Apparatus and Method for Delivering a Pharmaceutical Liquid to Form a Pharmaceutical Dosage.

* cited by examiner

*Primary Examiner* — Christopher Harmon
(74) *Attorney, Agent, or Firm* — Stephen H. Eland; Dann, Dorfman, Herrell & Skillman

(57) ABSTRACT

A capsule pressure control assembly for regulating or controlling the internal pressure of filled capsules, whereby instances of capsule elongation are reduced or eliminated, thus resulting in an increased yield rate of acceptable filled capsules.

20 Claims, 7 Drawing Sheets

APPARATUS AND METHODS FOR REDUCING CAPSULE ELONGATION

RELATED APPLICATIONS

This application claims priority to U.S. Provisional Patent Application No. 61/094,791 filed on Sep. 5, 2008. The entire disclosure of the foregoing application is incorporated herein by reference.

TECHNICAL FIELD

The present apparatus and method relate to preparing capsules and particularly to an apparatus and method for preparing pharmaceutical capsules in which the material filled into the capsules is above room temperature during the fill process. More specifically, the present method and apparatus are directed to reducing or preventing the elongation of capsules due to the thermal expansion of air contained within a filled capsule.

BACKGROUND INFORMATION

Capsules are typically used as a dosage form to deliver a variety of pharmaceutical compounds, dietary supplements and the like to a subject. The capsules generally include a body and a cap, with a fill material charged to the body portion. The cap fits over the body to enclose the fill material within the capsule. The cap and body engage one another by virtue of a locking mechanism. Several types of locking mechanisms are available such as a ridge mechanism, friction mechanism and pin mechanism. Elements of these locking mechanisms often include a pre-lock ridge, ventilation and a final lock ring.

The fill material can have any of a number of forms such as a liquid with solids in suspension therein, a powder, a hot melt, or pellets. In some instances, the fill material can be charged to the capsule body at room temperature, while in other cases the fill material is heated prior to being received by the capsule body where the cap and body can become unlocked. During the fill process, the capsule can become elongated, particularly when the fill material is heated above room temperature. Thus there is a need within the pharmaceutical, dietary and food industries to regulate or control the internal pressure of filled capsules whereby instances of capsule elongation are reduced or eliminated, thus resulting in an increased yield rate of acceptable filled capsules.

SUMMARY

A capsule pressure control assembly is provided for regulating the internal pressure of a capsule, the capsule pressure control assembly includes a support unit comprising a structural unit and one or more trays, where the structural unit supports the one or more trays. The support unit also includes a cooling device in fluid communication with the support unit.

A method of regulating an internal pressure of a capsule is provided where the method includes placing at least one capsule having a fill material contained therein into a capsule pressure control assembly, and subjecting the at least one capsule to a volume of air having a temperature that is less than that of the fill material.

A method of regulating an internal pressure of a capsule is provided, where the method includes encapsulating a fill material in a capsule; placing at least one capsule having a fill material contained therein into a capsule pressure control assembly; and subjecting the at least one capsule to a volume of air having a temperature that is less than that of the fill material.

A method of regulating an internal pressure of a capsule is provided, where the method includes placing a filled capsule into a metal detecting unit; placing at least one capsule having a fill material contained therein into a capsule pressure control assembly; and subjecting the at least one capsule to a volume of air having a temperature that is less than that of the fill material.

DESCRIPTION OF THE DRAWINGS

For purposes of illustration, the drawings show selected, representative structures, it being understood that the invention is not limited to the precise arrangements and instrumentalities shown.

Like reference characters denote like elements throughout the drawings.

DETAILED DESCRIPTION

Figure 1:
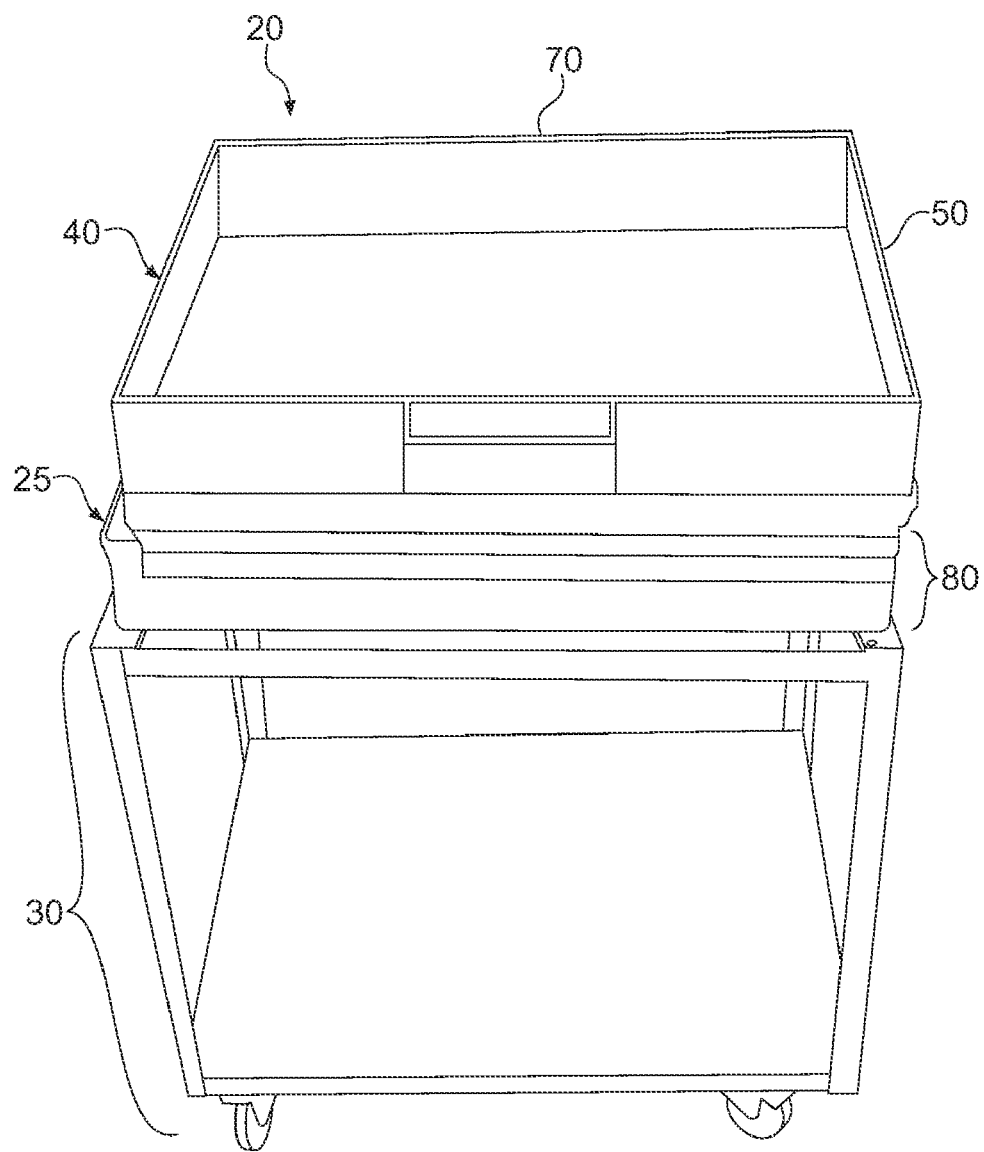
FIG. 1 is an elevated side view showing an embodiment of a capsule pressure control assembly.

It will be appreciated that the following description is intended to refer to specific representative structures selected for illustration in the drawings and is not intended to define or limit this disclosure, other than in the appended claims.

Figure 11:
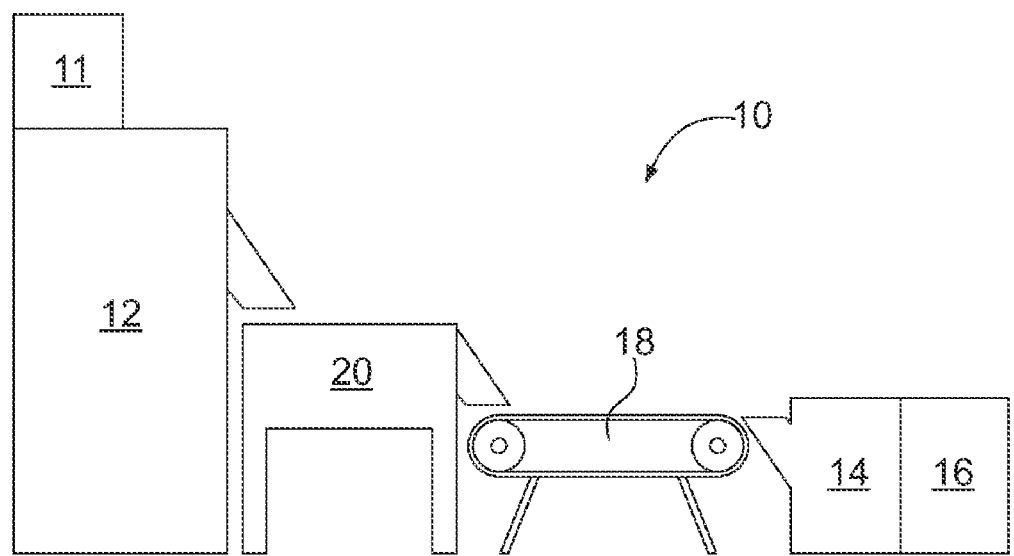
FIG. 11 is a schematic view of a system for filling capsules.

Referring now to the figures in general and to FIG. 11 specifically, a fill line for filling capsules is generally designated 10. The fill line 10 includes an encapsulator 12 for filling capsules with a fill material. The encapsulator may receive the fill material from a fluid delivery system 11 that includes a heating element for heating the fill material to an elevated temperature.

From the encapsulator 12, the capsules are processed by a capsule pressure control assembly 20 configured to reduce the internal pressure within the filled capsules. From the capsule pressure control assembly 20, the capsules may be transported to one or more capsule finishing elements. For instance, the capsule may be transported to a buffer/polisher 14 and/or a metal detector 16. The capsules may be automatically or manually conveyed between the different elements along the fill line For instance, the fill line 10 is illustrated as having a discharge for automatically discharging capsules from the encapsulator 10 to the capsule pressure control assembly 20, and a conveyor 18 for receiving the capsules from the capsule pressure control assembly and automatically conveying the capsules to the buffer/polisher 14 and or metal detector 16. Alternatively, the capsules may accumulate in an output container as they are processed by the encapsulator 12. An operator may then manually transport the capsules from the output container and feed the capsules to the capsule pressure control assembly 20. Similarly, the capsules from the capsule pressure control assembly may accumulate and then be manually transported to the buffer/polisher 14, so that the conveyor 18 would be unnecessary.

As used in the following description, "fill material" refers to the material that is filled into a capsule. A "filled capsule" refers to a capsule charged with fill material. Heated fill material is fill material that is heated to a temperature above room temperature when it is metered into the capsules.

The capsules may be sized so that the volume of the capsule is greater than the volume of the fill material, so that an air pocket is within the filled capsule. If the fill material is metered into the capsule while the fill material is at an elevated temperature, the fill material may transfer heat to air that may be entrapped within the capsule, causing the air to expand.

The fill material may be any of a number of forms such as a liquid with solids in suspension therein, a powder, a hot melt, or pellets. An exemplary heated fill material can be a hot molten melt comprising a polymeric material (polyethylene glycol (PEG)) which melts at a certain temperature (such as about 60° C. to about 70° C.), admixed with a pharmaceutically active agent (such as glycopeptide antibiotic), and excipients known in the art if desired. The pharmaceutically active agent can be dissolvable in the melted polymeric material, or it can form a suspension in the melted polymeric material. In certain applications, other polymeric materials may include polyalkylene (oxides) such as polyethylene glycol and propylene glycol, waxes such as paraffin, and polysaccharides of any suitable molecular weight. If PEG is used, suitable member average molecular weights include about 600, about 800, about 1000, about 3500, about 4000, about 6000, about 10,000 or about 100,000.

The capsule pressure control assembly 20 and its components can be used in conjunction with any capsule used in the pharmaceutical, dietary or food industries having a heated fill material charged thereto. The present description refers to pharmaceutical capsules for exemplary purposes only.

The capsule pressure control assembly 20 and the related components can comprise materials such as plastic, metal, wood, combinations of these materials and the like. In particular, the components comprise stainless steel.

Figure 2:
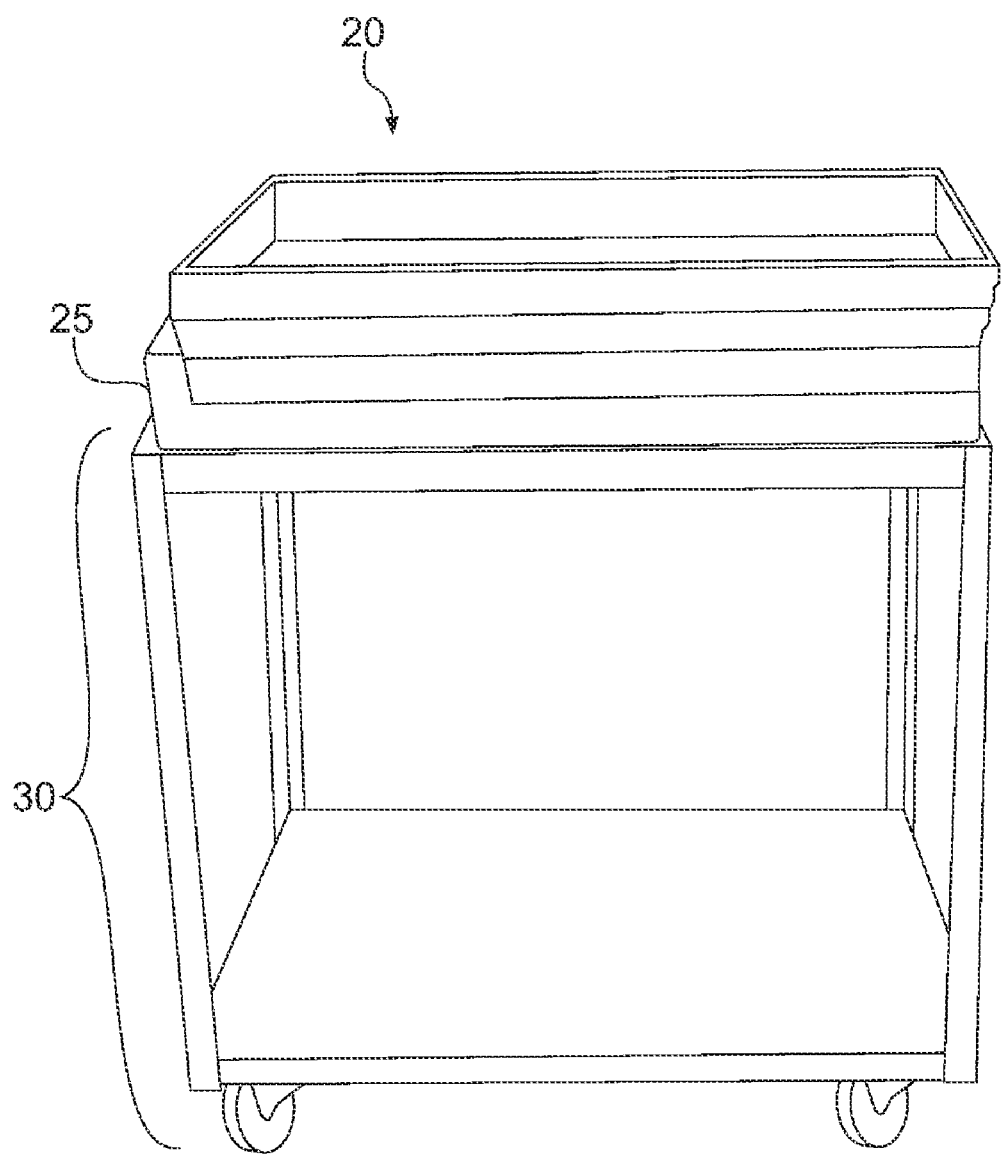
FIG. 2 is an elevated side view of an embodiment of a capsule pressure control assembly.
Figure 3:
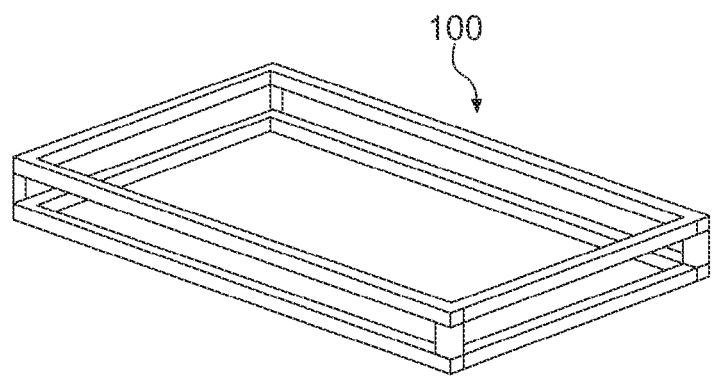
FIG. 3 is a perspective view of a frame for use in mounting an embodiment of a cooling element of the capsule pressure control assembly illustrated in FIG. 1.
Figure 4:
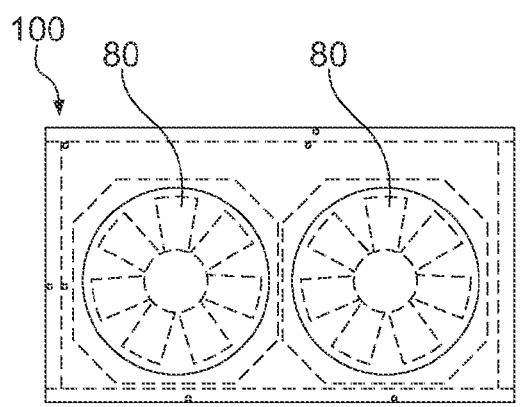
FIG. 4 is a top view of a cooling element and casing of the capsule pressure control assembly illustrated in FIG. 1.

FIGS. 1 and 2 illustrate an embodiment of a capsule pressure control assembly 20 that is capable of regulating or controlling the internal pressure of a capsule charged with heated fill material. As part of the process of forming capsules, the encapsulator fills each capsule with a quantity of fill material. During the encapsulation, a quantity of air may be entrapped within the capsule. When the fill material is a heated fill material, the fill material may heat the air entrapped with the capsule. The entrapped air may then expand causing capsule malformation. Specifically, thermal expansion of the entrapped air causes the internal pressure of the filled capsule to exceed the strength of the capsule's locking mechanism resulting in the elongation of the capsule's cap and body beyond the capsule's locking mechanism (i.e., the cap and body become unlocked).

The resulting malformed capsule impedes proper packaging during the automated packaging procedure. For instance, in the present instance, the capsules may be packaged into blister packages that have openings for receiving the capsule. Each capsule opening has a length or a diameter, depending on whether the opening is round or oblong. If the malformed capsule exceeds the length (or diameter) of the opening, the capsule will not fit into the opening, thus leading to an interruption in the packaging machinery. As a result labor-intensive methods are employed to pre-inspect the filled capsules to remove the elongated capsules prior to entering the packaging machinery.

Referring to FIGS. 2-7, the capsule pressure control assembly 20 comprises a support unit 25 and a capsule cooling device 80. The cooling device 80 is in fluid communication (either directly or indirectly) with the support unit 25 as described below.

Figure 6:
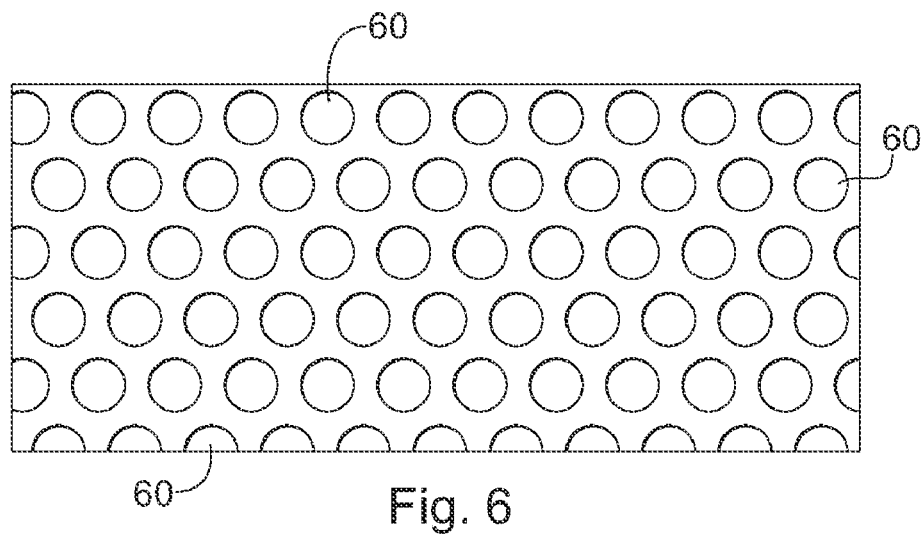
FIG. 6 is an enlarged fragmentary view of the floor of a tray of the capsule pressure control assembly illustrated in FIG. 1.
Figure 7:
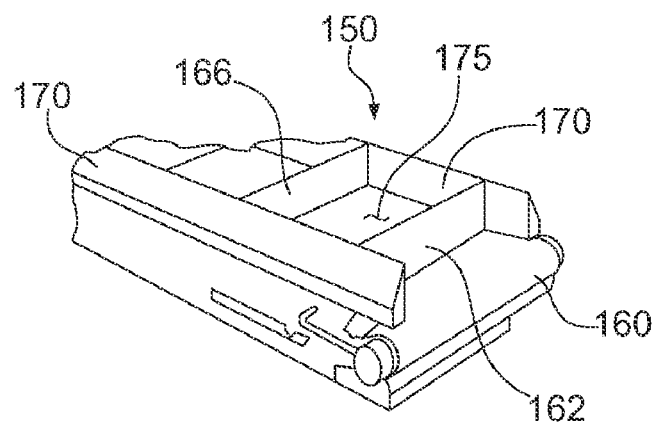
FIG. 7 is a fragmentary perspective view of an alternate embodiment of a capsule pressure control assembly.

The support unit 25 comprises a structural unit 30 and a tray 40 capable of containing at least one capsule. The tray 40 comprises a floor 50 and walls 70 extending substantially upward away from the floor to contain the filled capsules. The floor 50 provides a surface onto which the filled capsules are dispersed for cooling. The floor 50 can have any number of configurations so long as it permits air flow past the filled capsules. For example, as shown in FIG. 6, the floor 50 can comprise one or more of slits, slots, holes or other type of orifice 60 that allows the movement of cooling air where the air can flow out of the orifice or can be drawn therethrough. The floor 50 can comprise a mesh that allows air to easily flow among and around the capsules. The orifice or mesh size need not be limited to a particular size so long as it is capable of retaining the capsules thereon and permitting a volume of air to circulate. A suitable mesh or orifice would include one in which a capsule having its major axis oriented parallel or perpendicular to the plane of the tray floor 50 would not pass through the mesh while also permitting a level of air flow capable of reducing the internal pressure of the capsules. As an example, a suitable orifice for use with either a 125 mg or 250 mg VANCOCIN® capsule (both available from ViroPharma Incorporated, Exton, Pa.), (capsule sizes 2 and 0, respectively) would have a diameter less than or equal to about ¼ inches (0.25 inches) and, in particular, would be about ⅛$^{th}$ inches in diameter, in an offset pattern. A suitable mesh size for use with either a 125 mg or 250 mg VANCOCIN® capsule (both available from ViroPharma Incorporated, Exton, Pa.) can have a size of less than or equal to about ¼ inch (0.25 inches). In particular, the mesh size can range from about ¼ inch (0.25 inches) to about a size 14 mesh.

Alternatively or in addition to the forced air described above, the tray 40 can be refrigerated to lower its surface temperature to aid in regulating the internal pressure of the filled capsules. In yet another alternative, the tray can be supplied with cooled water, air or other gas that circulates via a network of internal passage ways. If the tray is refrigerated or otherwise cooled, the temperature of the tray should be regulated to minimize the formation of tray surface condensation.

In the present instance, the capsules are substantially evenly distributed across the tray floor 50 (referred to as a capsule layer) to assist in maximizing each capsule's exposure to the volume of air. The capsule layer also helps to avoid capsule clumping or clusters, which can retain heat. Typically the capsule layer has a depth no greater than approximately five capsules, however more than five layers is permissible.

The structural unit 30 provides support for one or more trays 40, and optionally the cooling device 80, where each is an individual and independent component. Each tray 40 can be removably engaged with the structural unit 30. For example, the one or more trays 40 can slide along rails such that the one or more trays 40 can be easily inserted or removed from the structural unit 30 (i.e., stacking one or more trays in a racking system). The structural unit 30 can also serve as a frame for one or more trays 40 wherein the trays 40 can sit within the framework to provide a stable surface onto which the filled capsules can be discharged. The structural unit 30, the one or more trays 40, and optionally the cooling device 80, can also be integrated with one another, whereby they are a single unit. The one or more trays 40 can be securely engaged with the structural unit 30 using any method known to one skilled in the art such as, for example, welding, bolts, screws and the like. The structural unit 30 can be either portable (i.e., lightweight or mounted on wheels such as a cart) or non-portable (i.e., a permanently affixed structure or the conveyor system described below).

The support unit 25 can be an automated component in the capsule fill line 10, such as a conveyor system. For example, filled capsules can be discharged from the encapsulator or polisher/sorter and onto a tray such as a mesh conveyor belt having one or more cooling device mounted below, which draws air past the filled capsules. Alternatively, the conveyor belt can travel through a cooling tunnel where a volume of cooling air is supplied to create a cool environment for the filled capsules. The cooling tunnel can provide the volume of air using one or more cooling devices 80. Conveyor length can be adjusted to correspond to the required cooling time and/or available space.

The support unit 25 may be a manual component in the capsule fill line 10 such as, for example, a cart having a tray 40 thereon. An operator can manually place the filled capsules onto the tray 40 or the filled capsules can be discharged from the encapsulator or polisher/sorter directly on the tray 40. The operator can transfer the filled capsules to another capsule pressure regulating assembly 20 or to the polisher/sorter unit or other unit used as the next component of the capsule fill process.

In the present instance, the support unit 25 is capable of accepting the cooling device 80, which is capable of providing air to sufficiently control the filled capsule's internal pressure to reduce or eliminate capsule malformation. The use of a portable support unit 25 allows an operator to cool the filled capsules and move the capsules between various components of the capsule fill line where an automated method of doing so would not be feasible or desirable. Alternatively, the support unit 25 can be a structure that is non-portable, whereby the tray 40 can be lifted or otherwise removed from the structural unit 30. The cooling device 80 can be mounted onto either the structural unit 30 itself (if the tray and structural unit are integrated as a single unit) or the cooling device can be mounted to either the structural unit 30 or tray 40 if they are individual components.

The support unit 25 can have the cooling device 80 mounted thereon in a removable fashion (i.e., clamps) or a more permanent fashion (i.e., welding). The cooling device 80 should be mounted such that it is capable of providing the necessary volume of air to the filled capsules.

The cooling device 80 can be any device capable of exposing the filled capsules to a volume of air capable of reducing or eliminating capsule elongation. The volume of air can be blown past the filled capsules or drawn past the filled capsules (for example by a fan or vacuum). A single cooling device 80 can be used or multiple cooling devices 80 can be used.

The filled capsules can be directly exposed to the volume of air by blowing or drawing air around the capsules and through the floor 50 of the tray 40. Alternatively, the capsules can be indirectly exposed to the volume of air by exposing the capsules to a pre-cooled environment such as an air conditioned chamber.

Figure 5:
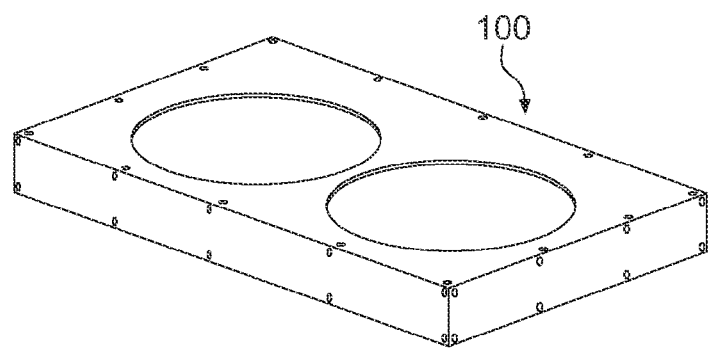
FIG. 5 is a perspective view of the casing of the cooling element illustrated in FIG. 4.

Exemplary cooling devices 80 include, but are not limited to, one or more fans or a custom cooling tunnel having a perforated belt. For example, two (2) 120VAC fans can be used, each having an air flow rating of about 1100 CFM (total air flow of about 2200CFM) (Model No. W2E250-HJ32-01, available from Ebmpapst) enclosed and mounted in a stainless steel case 100 (as shown in FIG. 5) mounted on the underside of the tray 40 or on the support unit 25. The fan can further be combined with an air conditioning unit or the like to provide air of various temperatures.

The cooling device 80 can be located in close proximity to the filled capsules. For example, the cooling device 80 can be mounted on the support unit 25 and positioned above or below the tray 40. Alternatively the cooling device 80 can be located remotely from the filled capsules, where the volume of air is supplied via pipes, hoses and the like. For example, the cooling device can be located in the ceiling, wall or a different room entirely.

As noted above, controlling the internal pressure of the filled capsules is effectuated by exposing the capsules to a volume of air. The volume of air can differ based upon a number of variables including, but not limited to, the size of the capsule, the number of capsules, the temperature of the fill material, and/or the temperature of the volume of air.

The volume of air can also be drawn from ambient air if such ambient air satisfies parameters, such as those described below, for sufficiently cooling the filled capsules, for example where the ambient air is drawn from a room where the air quality, temperature and humidity are controlled. Alternatively, suitable externally provided air can be utilized so long as the air quality, temperature and humidity are controlled. The air can be filtered (for example using a HEPA filter) to ensure no contaminants are introduced to the capsules. The temperature of the volume of air can range from about 10° C. to about 60° C. Preferably the temperature of the volume of air ranges from about 10° C. to about 30° C., more preferably ranging from about 16° C. to about 25° C.

The relative humidity of the volume of air can range from about 10% to about 50%. Preferably the relative humidity of the volume of air ranges from about 15% to about 45%, more preferably ranging from about 20% to about 40%.

The filled capsules can be exposed to a volume of air ranging from about 100 cubic feet/minute (CFM) to about 3000 CFM. Preferably the capsules are exposed to a volume of air ranging from about 1000 CFM to about 2500 CFM, more preferably from about 2000 CFM to about 2500 CFM and most preferable about 2200 CFM.

The filled capsules are generally exposed to the volume of air for at least about 3 minutes. However, the filled capsules can be cooled for at least about 5 minutes, at least about 10 minutes or even at least about 20 minutes. The cooling time can be adjusted based upon, among others, the total number of capsules being cooled, the rate of encapsulation (capsules filled/minute), and/or the number of capsule layers. Optionally, additional cooling can also be performed, simply exposing the filled capsules to the ambient air for a time ranging from about 10 minutes to about 5 hours.

As noted above, thermal expansion of the entrapped air results in increased internal capsule pressure. For example, initially upon encapsulation, the entrapped air in a filled capsule has a pressure of about 1 Atmosphere (0 psig). However, upon heat exchange the internal pressure could reach about 1.17 Atmospheres (2.49 psig), the pressure could overcome the capsule locking mechanism. Thus, embodiments of the capsule pressure control assembly 20 regulate or control the filled capsule's internal pressure so that upon thermal expansion the internal pressure remains below approximately 1.17 Atmospheres (2.49 psig), and in particular it remains at approximately 1 Atmosphere (0 psig).

Excessive capsule elongation prevents the filled capsule from being properly packaged in a blister card configuration. Prior to undergoing any thermal expansion, a filled capsule will have a predetermined length, which depends upon the size of the capsule utilized. Due to increased internal pressure, the filled capsule may become elongated to where its increased length renders it unacceptable for packaging. For example, the filled capsule for the 250 mg VANCOCIN® capsule product (available from ViroPharma Incorporated, Exton, Pa.) may range in length from about 21.5 mm to about 22.0 mm (typically about 21.7 mm). An elongated form of this capsule typically has a length greater than about 22.7 mm. Thus if a 250 mg capsule increases in length by more than about 3% to about 6%, it may be rejected. Employing the capsule pressure control assembly 20 limited elongation to no more than approximately 3% to approximately 6% of the overall capsule length. Likewise, the filled capsule for the 125 mg VANCOCIN® capsule product (available from ViroPharma Incorporated, Exton, Pa.) can range in length from about 17.8 mm to about 18.1 mm. An elongated form of this capsule typically has a length greater than about 18.7 mm. Thus if the capsule increase in length more than approximately 3% to approximately 5% the capsule is rejected. Employing the capsule pressure control assembly 20 limited elongation to no more than about 3% of the overall capsule length. Thus, the capsule pressure control assembly 20 regulates or controls the internal pressure of at least one filled capsule by lowering the temperature of the entrapped air, thereby reducing or eliminating instances of capsule elongation. As a result of the capsule pressure control assembly 20, there is an increase in the overall yield rate of filled capsules that are acceptable for packaging.

Referring again to FIG. 11, the fill line includes an encapsulator 12. An exemplary encapsulator is the Bosch 1400 L Liquid Encapsulation Machine, available from Bosch Packaging Technology, Brooklyn Park, Minn.). In the present instance, the fill line also includes a polishing/sorting station. An exemplary polishing/sorting station is the Turbo-Kleen, Model No. CP-350, available from Key International, Englishtown, N.J.). Additionally, in the present instance, the fill line 10 includes a metal detector such as a Safeline Model 063 Version 1.251, available from Mettler-Toledo Safeline, Tampa, Fla.).

The capsule pressure control assembly 20 can be positioned at several locations in the capsule fill line. For example, one suitable position for an embodiment of the capsule pressure control assembly 20 is after the metal detection unit 16, such that capsules are discharged from the metal detector and to the capsule pressure control assembly and cooled as described above. Another suitable position for an embodiment of the capsule pressure control assembly 20 is after the encapsulator unit 12, as shown in FIG. 11, such that capsules are discharged from the encapsulator unit and to the capsule pressure control assembly and cooled as described above. Still further, more than one capsule pressure control assembly 20 can be used at a particular location in the capsule fill line (for example, two of the same or different embodiments positioned after the encapsulator 12 or at different locations in the capsule fill line (for example, one or more embodiments of the capsule pressure control assembly positioned after the encapsulator and the polisher/sorter).

Configured as described above, an exemplary method is operable as follows. The encapsulator meters a fill material into the body of the capsule and engages the cap with the body to form the filled capsule. Once the fill material is received by the capsule body and the cap is placed thereon, the fill material begins to heat any entrapped air. The filled capsule is discharged from the encapsulator and received onto the tray of a capsule pressure control assembly 20. The filled capsule is exposed to a volume of air for a pre-defined length of time to reduce the internal pressure. Optionally, the filled capsule can be received onto the tray of any number of consecutive capsule pressure control assemblies and again exposed to a volume of air for a pre-defined length of time. The filled capsule travels to the polisher/sorter unit, which acts to improve the appearance of the capsule through polishing the exterior, and removing any fill material thereon as well as any empty, broken or separated capsules. Optionally, the filled capsule can be received onto the tray of any number of consecutive capsule pressure control assemblies and again exposed to a volume of air for a pre-defined length of time. The filled capsule undergoes metal detection, where a metal detecting unit serves to determine whether any metal shavings or particles have gotten into a filled capsule. As a result of the one or more capsule pressure control assemblies reducing or eliminating capsule elongation, there is an increased yield rate of non-rejected filled capsules.

EXAMPLES

In Examples 1 and 4, two capsule pressure control assemblies were utilized, where each capsule pressure control assembly included two (2) 120VAC fans, each having an air flow rating of about 1100 CFM (Model No. W2E250-HJ32-01, available from Ebmpapst). Each capsule pressure control assembly was positioned immediately after the discharge of a Bosch 1400 L Liquid Encapsulation Machine (available from Bosch Packaging Technology, Brooklyn Park, Minn.). As capsules were discharged from the encapsulation machine, the filled capsules were collected in a perforated tray (the tray having offset orifices of about ⅛ inches in diameter) having the two fans mounted thereunder pulling air past the filled capsules. The filled capsules were subjected to a first capsule pressure control assembly 20 for 10 minutes prior to passing through the capsule polisher/sorter and metal detector units. After 10 minutes the tray was moved to a second capsule pressure control assembly 20 where the filled capsules cooled for another 10 minutes. Thus, cooling time was approximately 19 minutes and 59 seconds for the first capsule discharged onto the tray, and approximately 10 minutes and 1 second for the last capsule discharged onto the tray. After the second 10 minute cooling period was completed, the filled capsules were manually scooped into the capsule polisher/sorter and metal detector. Subsequent to passing through the polisher/sorting unit and metal detector, the capsules where again discharged onto a tray. The tray was placed on a cooling rack for further cooling and congealing for about 4 hours after the last tray was placed into the cooling rack. The Control batch (Tray 1) was executed without utilizing the capsule pressure control assembly to determine an approximate base line level of capsule rejection (due to capsule elongation). A sample of 100 capsules was taken from each of the trays. The capsules from each of the sample groups were measured by placing each sample group into a shaker tray. The shaker tray had an interior void dimension of 22.2-22.3 mm and was used to determine the number of elongated filled capsule shells. The number of elongated filled capsule shells was counted and recorded.

In Examples 2 and 3, only a single capsule pressure control assembly was used, which included two (2) 120VAC fans, each having an air flow rating of about 1100 CFM (Model No. W2E250-HJ32-01, available from Ebmpapst). The capsule pressure control assembly was positioned immediately after the discharge of a Bosch 1400 L Liquid Encapsulation Machine (available from Bosch Packaging Technology, Brooklyn Park, Minn.). As capsules were discharged from the encapsulation machine, the filled capsules were collected in a perforated tray (the tray having offset orifices of about ⅛ inches in diameter) having the two fans mounted thereunder pulling air past the filled capsules. The filled capsules were subjected to the capsule pressure control assembly for approximately 10 minutes prior to passing through the capsule polisher/sorter and metal detector units. After the cooling period was completed, the filled capsules were manually scooped into the capsule polisher/sorter and metal detector. Subsequent to passing through the polisher/sorting unit and metal detector, the capsules where again discharged onto a tray. The tray was placed on a cooling rack for further cooling and congealing for about 4 hours after the last tray was placed into the cooling rack. The Control batch (Tray 1) was processed without utilizing the capsule pressure control assembly to determine an approximate base line level of capsule rejection (due to capsule elongation). A sample of 100 capsules was taken from each of the trays. The capsules from each of the sample groups were measured by placing each sample group into a shaker tray.

The shaker tray had an interior void dimension of 22.2-22.3 mm for the 250 mg capsules and 18.2 mm for the 125 mg capsules, and was used to determine the number of elongated filled capsule shells. The number of elongated filled capsule shells was counted and recorded

Example 1

VANCOCIN HCl 250 mg Capsule Results (Post-Encapsulation Pressure Control)

In Example 1, the ambient air in the controlled environment was used for pressure controlling purposes. At the start of the process to produce capsules used in Example 1, the air had a temperature of 18° C. and a relative humidity of 28%. The molten fill had a temperature of 66.6° C. The controlled environment was equipped with alarms to provide a signal if the ambient room temperature did not remain between 16-25° C., with a relative humidity between 20% and 40%. As shown in Table 1, the Control batch had a total of 64 capsules determined to be elongated and were thus rejected. Subsequent capsule sample groups (Groups 2-37) utilizing the capsule pressure control assembly had only a single rejection due to an elongated capsule (Tray #12). As a result of the capsule pressure control assembly the occurrence of elongated capsules was reduced from 64% to below 0.5%. Based on the results shown in Table 1, the yield rate for non-rejected capsules increased from 36% (36 non-rejected capsules out of a total of 100) to 99.9% (3599 non-rejected filled capsules out of a total of 3600).

TABLE 1

| VANCOCIN HCl 250 mg Capsules | |
|---|---|
| Tray (#) | No. of Elongated Capsules |
| 1 (Control) | 64 |
| 2 | 0 |

TABLE 1-continued

| VANCOCIN HCl 250 mg Capsules | |
|---|---|
| Tray (#) | No. of Elongated Capsules |
| 3 | 0 |
| 4 | 0 |
| 5 | 0 |
| 6 | 0 |
| 7 | 0 |
| 8 | 0 |
| 9 | 0 |
| 10 | 0 |
| 11 | 0 |
| 12 | 1 |
| 13 | 0 |
| 14 | 0 |
| 15 | 0 |
| 16 | 0 |
| 17 | 0 |
| 18 | 0 |
| 19 | 0 |
| 20 | 0 |
| 21 | 0 |
| 22 | 0 |
| 23 | 0 |
| 24 | 0 |
| 25 | 0 |
| 26 | 0 |
| 27 | 0 |
| 28 | 0 |
| 29 | 0 |
| 30 | 0 |
| 31 | 0 |
| 32 | 0 |
| 33 | 0 |
| 34 | 0 |
| 35 | 0 |
| 36 | 0 |
| 37 | 0 |

Example 2

VANCOCIN HCl 125 mg Capsule Results (Post-Encapsulation Pressure Control)

In Example 2, the ambient air in the controlled environment was used for pressure controlling purposes. At the start of the process to produce capsules used in Example 2 the air had a temperature of 18° C., and a relative humidity of 29%. The temperature of the hot melt during encapsulation was 67.7° C. The controlled environment was equipped with alarms to provide a signal if the ambient room temperature did not remain between 16-25° C., with a relative humidity between 20% and 40%. As shown in Table 2, the Control batch (Tray #1) had 1 capsule determined to be elongated and was thus rejected. Subsequent capsule sample groups (Groups 2-13) utilizing the capsule pressure control assembly had zero rejections due to elongated capsules. As a result of the capsule pressure control assembly the occurrence of elongated capsules was reduced from 1% to 0%. Based on the results shown in Table 1, the yield rate for non-rejected capsules increased from 99% (99 non-rejected capsules out of a total of 100) to 100% (1300 non-rejected filled capsules out of a total of 1300).

TABLE 2

VANCOCIN HCL 125 mg Capsules

| Tray (#) | No. of Elongated Capsules |
| --- | --- |
| 1 (Control) | 1 |
| 2 | 0 |
| 3 | 0 |
| 4 | 0 |
| 5 | 0 |
| 6 | 0 |
| 7 | 0 |
| 8 | 0 |
| 9 | 0 |
| 10 | 0 |
| 11 | 0 |
| 12 | 0 |
| 13 | 0 |

Example 3

VANCOCIN HCl 250 mg Capsule Results (Post-Encapsulation Pressure Control)

In Example 3, the ambient air in the controlled environment was used for cooling purposes. At the start of the process to produce capsules used in this Example 3, the air had a temperature of 17° C., and a relative humidity of 30%. The temperature of the hot melt during encapsulation was 66.4° C. The controlled environment was equipped with alarms to provide a signal if the ambient room temperature did not remain between 16-25° C., with a relative humidity between 20% and 40%. As shown in Table 3, the Control batch had a total of 28 capsules determined to be elongated and were thus rejected. Subsequent capsule sample groups (Groups 2-22) utilizing the capsule pressure control assembly had zero rejections due to elongated capsules. As a result of the capsule pressure control assembly the occurrence of elongated capsules was reduced from 28% to 0%. Based on the results shown in Table 3, the yield rate for non-rejected capsules increased from 72% (72 non-rejected capsules out of a total of 100) to 100% (2200 non-rejected filled capsules out of a total of 2200).

TABLE 3

VANCOCIN HCL 250 mg Capsules

| Tray (#) | No. of Elongated Capsules |
| --- | --- |
| 1 (Control) | 28 |
| 2 | 0 |
| 3 | 0 |
| 4 | 0 |
| 5 | 0 |
| 6 | 0 |
| 7 | 0 |
| 8 | 0 |
| 9 | 0 |
| 10 | 0 |
| 11 | 0 |
| 12 | 0 |
| 13 | 0 |
| 14 | 0 |
| 15 | 0 |
| 16 | 0 |
| 17 | 0 |
| 18 | 0 |
| 19 | 0 |
| 20 | 0 |
| 21 | 0 |
| 22 | 0 |

Example 4

VANCOCIN HCL 125 mg Capsule Results (Post-Encapsulation Pressure Control)

In Example 4, the ambient air in the controlled environment was used for cooling purposes. At the start of the process to produce capsules used in this Example, the air had a temperature of 18° C., and a relative humidity of 29%. The temperature of the hot melt during encapsulation was 67.2° C. The controlled environment was equipped with alarms to provide a signal if the ambient room temperature did not remain between 16-25° C., with a relative humidity between 20% and 40%. As shown in Table 4, the Control batch had zero rejections due to elongated capsules. Subsequent capsule sample groups (Groups 2-1) utilizing the capsule pressure control assembly also had zero rejections due to elongated capsules.

TABLE 4

VANCOCIN HCL 125 mg Capsules

| Tray (#) | No. of Elongated Capsules |
| --- | --- |
| 1 (Control) | 0 |
| 2 | 0 |
| 3 | 0 |
| 4 | 0 |
| 5 | 0 |
| 6 | 0 |
| 7 | 0 |
| 8 | 0 |
| 9 | 0 |
| 10 | 0 |
| 11 | 0 |
| 12 | 0 |
| 13 | 0 |

Referring now to FIGS. 8-11 a capsule pressure control conveyor 150 is illustrated. The conveyor 150 conveys the capsules along a pathway configured to process the capsules to reduce any elevated pressure in the capsules that may lead to malformation. As such, the conveyor 150 can be utilized in the fill line 10 illustrated in FIG. 11 in place of the capsule pressure control assembly 20 described above. As with the capsule pressure control assembly 20 discussed above the conveyor 150 may be mounted on a portable support, such as a cart so that the conveyor can be moved into position adjacent an output of the encapsulating system 12 if desired or moved away from the encapsulating system if it is not desired for processing a particular batch of capsules.

The capsule pressure control conveyor 150 has an input end 152 at which capsules are loaded onto the conveyor from the encapsulator 12. The capsules may be manually dumped onto the conveyor at the input 152, however, in the present instance, a chute directs capsules onto the conveyor input directly from the encapsulator 12. The conveyor 150 conveys the capsules through a cooling zone that reduces the internal pressure that has built up in the capsules. The capsules are then discharged from the conveyor 150 at a discharge end 154 remote from the input 152.

The conveyor 150 comprises an endless conveyor belt 160 entrained about a plurality of pulleys 167. The pulleys are laterally adjustable so that the position of the pulleys can be varied to increase or decrease the tension on the conveyor belt 160. A drive shaft 168 extending through one of the pulleys 167 drives the conveyor belt 160. The drive shaft is driven by a power source such as a motor.

A variety of belt configurations can be used depending upon the type of cooling zone used. For instance, in the present instance, the capsule pressure control conveyor uses forced air convection to cool the capsules. Accordingly, the conveyor belt 160 is configured to facilitate air flow through the conveyor to force air over the capsules on the conveyor. For instance, the conveyor may be a generally flat belt having perforations. If a perforated belt is used, then preferably the perforations are sized similarly to the perforations discussed above in connection with the perforated tray for the capsule pressure control assembly 20. Alternatively, the conveyor belt 160 make be a link belt formed of a plurality of interlocking links having perforations through the thickness of the belt to facilitate airflow through the belt.

Figure 12:
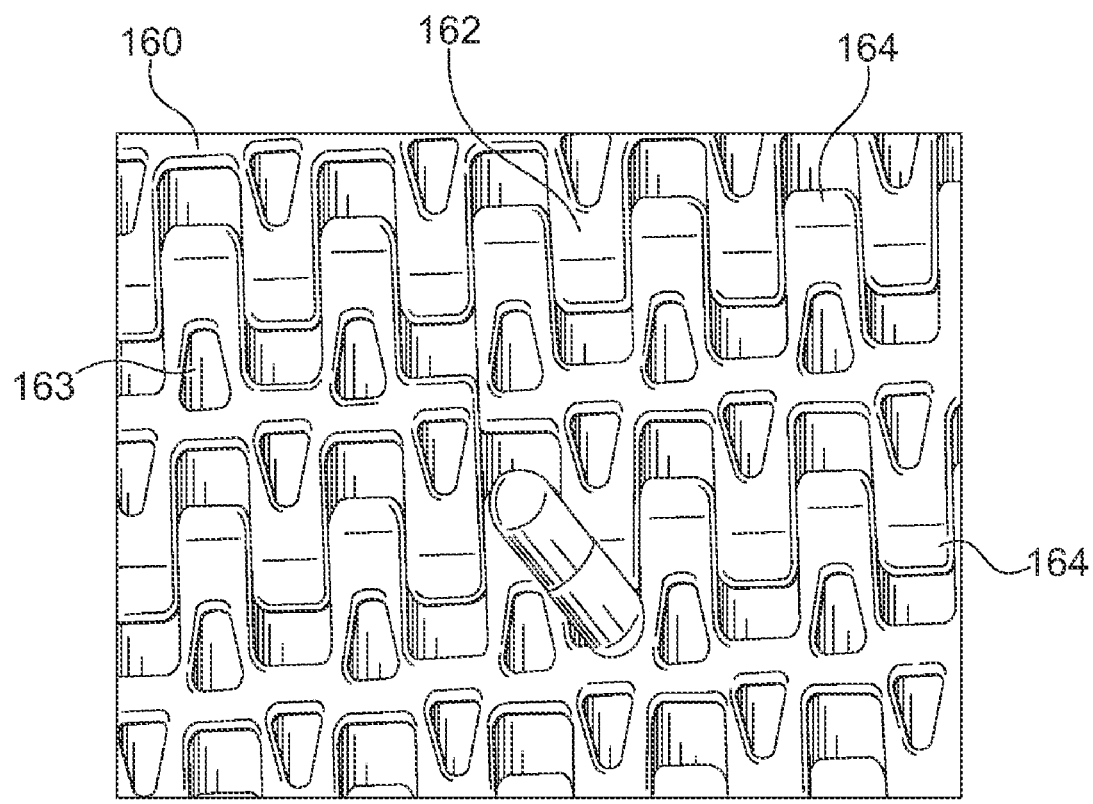
FIG. 12 is fragmentary view of a portion of the belt of the conveyor illustrated in FIG. 8.

Referring to FIG. 12, in the present instance, the belt is formed of a plurality of links 162. The links may be formed of a variety of materials, such as metal, ceramic or polymer. In the present instance, the links 162 are formed of plastic, such as acetal or polypropylene. The links 162 include a plurality of openings 163 through the thickness of the links to form an open mesh or grate to allow air flow through the belt. The links extend across the width of the belt and are connected to one another by connectors to form a continuous loop. More specifically, the links 162 comprise connectors in the form of aligned holes across the width of the belt that provide a pivot axis between adjacent links. A connector, such as a hinge pin extends through the aligned holes in the adjacent links to pivotably connect the links.

The conveyor 150 includes a pair of generally parallel side walls 170 that extend along substantially the entire length of the top run of the conveyor belt 160. The side wall are laterally spaced apart from one another and the side edges of the conveyor belt 160 pass under the side walls 170, so that the conveyor belt spans the entire distance between the sidewalls. In the present instance, the conveyor belt 160 either engages the underside of the side walls 170 or is spaced apart from the sidewalls by a distance substantially less than the width or thickness of the capsules to impede capsules from passing between the conveyor belt and the side walls. Accordingly, the side walls 170 operate as guides or constraints that retain the capsules on the belt 160 as the capsules are conveyed from the input 152 to the discharge 154.

Although the conveyor 150 may utilize any of a variety of flat belts, in the present instance, the belt 160 is a flat belt including a plurality of partitions 166 that project upwardly from the surface of the belt. The partitions 166 extend laterally across substantially the entire width of the belt. However, in the present instance, the partitions 166 have a transverse width that is substantially the same as the distance between the sidewalls 170. Accordingly, the partitions project upwardly from the surface of the belt, extending between the side walls 170. The partitions are spaced apart from one another along the length of the conveyor belt, and in the present instance, the partitions 166 are substantially equally spaced apart from one another along the length of the conveyor belt.

Figure 10:
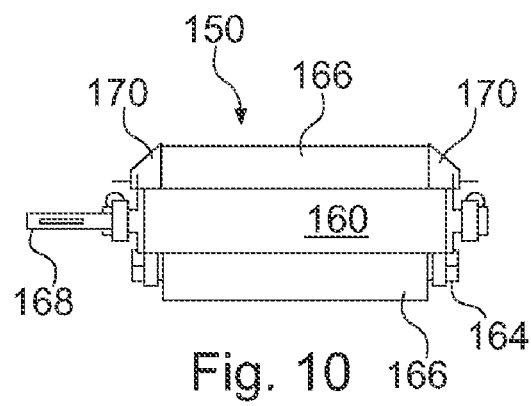
FIG. 10 is a front elevational view of the capsule pressure control assembly illustrated in FIG. 8.

Referring to FIG. 10, the partitions 166 and the side walls 170 form a plurality of receptacles 175 along the length of the belt from the input 152 to the discharge 154. Specifically, the forward and rearward wall of each receptacle is formed by two adjacent partitions. The conveyor side walls 170 form the side walls of the partitions. In the present instance, the partitions extend substantially the entire distance between the sidewalls so that little or gap is formed between the side edges of the partitions and the side walls 170, so that capsules do not mistakenly pass between the partitions and the side walls 170.

The receptacles 175 provide separate areas for receiving a quantity of capsules. By configuring the belt to provide a plurality of receptacles, the amount of capsules in a given area of the conveyor can more easily be controlled because the partitions 166 constrain longitudinal movement of the capsules along the length of the belt and the sidewalls constrain lateral movement of the capsules across the width of the belt. Additionally, the partition may operate as pushers to force the capsules toward the discharge as the conveyor drives forwardly.

Figure 8:
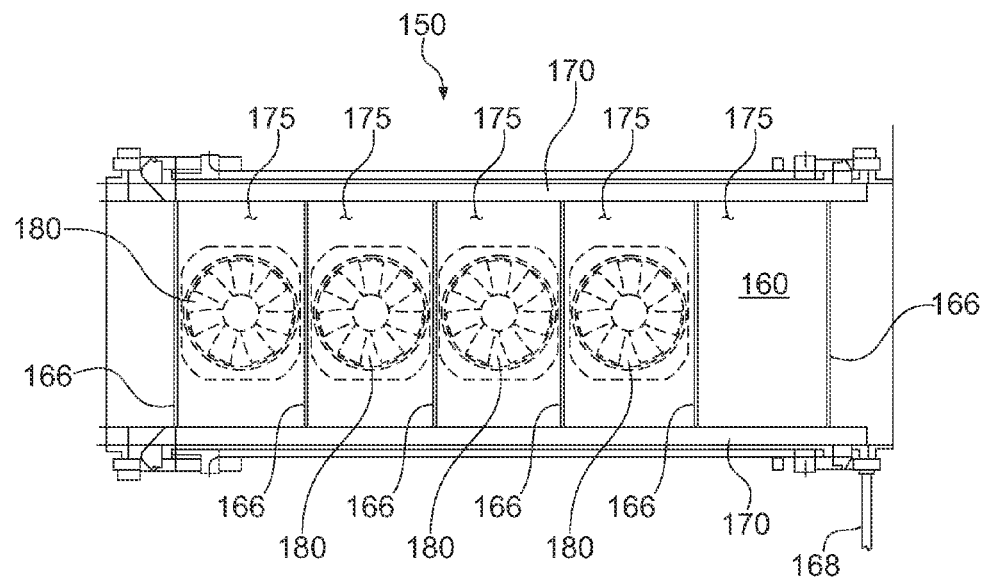
FIG. 8 is a plan view of the capsule pressure control assembly illustrated in FIG. 7.
Figure 9:
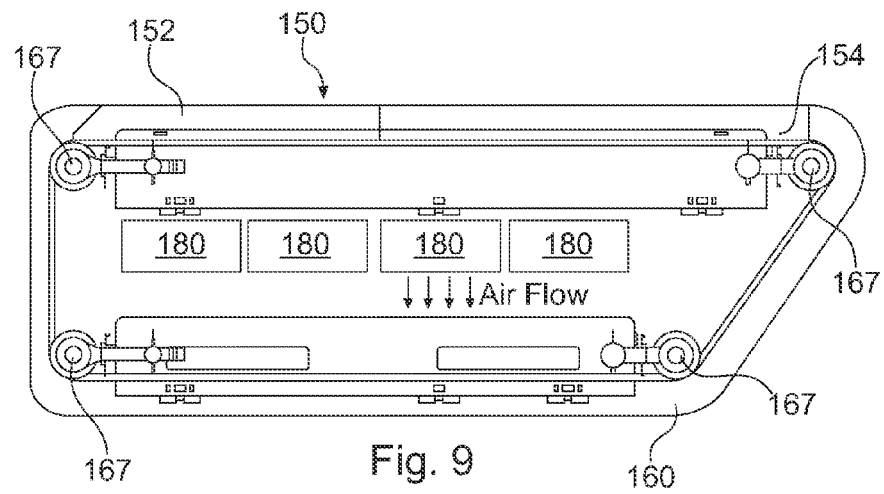
FIG. 9 is a side elevational view of the capsule pressure control assembly illustrated in FIG. 8.

As the conveyor 150 drives the capsules forwardly toward the discharge, the capsules pass through a cooling zone. The cooling zone may utilize any of a plurality of cooling elements. For instance, the conveyor may pass through a refrigeration section in which a refrigeration element is substantially cooler than ambient air (such as 20-60 degrees F.). Alternatively, in the present instance, the cooling zone comprises one or more elements for providing forced air convection for the capsules. Specifically, the cooling zone comprises a plurality of fans 180 for forcing air across the capsules as the capsules are conveyed along the length of the conveyor 150. The fans 180 can be configured to blow upwardly to force air upwardly toward the capsules. However, in the present instance, the fans 180 are configured to blow downwardly to pull air downwardly over the capsules. In this way, the flow of air from the fans will tend to draw the capsules toward the conveyor rather than blowing the capsules upwardly away from the conveyor. As shown in FIGS. 8-9, in the present instance, the cooling zone comprises a series of fans disposed along a substantial portion of the length of the conveyor 150. Specifically, in the present instance, the cooling fans extend along approximately ⅔ the length of the conveyor 150.

The speed of the conveyor is matched to the period of time it takes to substantially cool the capsules sufficiently to reduce elevated internal pressure in the capsules that could exceed the threshold latching force of the capsule latching mechanism. In the present instance, the capsules are loaded onto the conveyor 150 at a rate that provides a layer of capsules that is approximately 5 capsules or less deep in each receptacle with the quantity of capsules extending over substantially the entire area of the receptacle. Additionally, the conveyor is approximately 72 inches long and the conveyor speed is set to approximately 0.08 inch/sec so that the capsules are on the conveyor approximately 15 minutes from the time the capsules are loaded onto the input 152 to the time the capsules are discharge at the discharge 154.

The invention claimed is:

1. A capsule pressure control assembly for lowering the internal pressure of a capsule, the capsule pressure control assembly comprising:
a support unit configured to cooperate with the discharge of an encapsulating machine to receive capsule containing medicine in a melted polymeric matrix at a temperature substantially higher than ambient temperature for the assembly, wherein the support unit comprises a structural unit and one or more trays having a fluid permeable floor and sidewalls, wherein the structural unit supports the one or more trays; and
a cooling device in fluid communication with said support unit operable to drive a flow of fluid through the permeable floor of the trays to impede expansion of air in the matrix in the capsules following discharge of the capsules from the encapsulating machine.

2. The capsule pressure control assembly according to claim 1, wherein the structural unit is a cart.

3. The capsule pressure control assembly according to claim 1, wherein the tray floor is a mesh.

4. The capsule pressure control assembly according to claim 1, wherein the cooling device is mounted on the structural unit.

5. The capsule pressure control assembly according to claim 1, wherein the cooling device is a fan where a volume of air is drawn past at least one filled capsule.

6. The capsule pressure control assembly according to claim 5, wherein the volume of air ranges from about 100 CFM to about 3000 CFM.

7. The capsule pressure control assembly according to claim 5, wherein the volume of air has a temperature ranging from about 10° C. to about 60° C.

8. The capsule pressure control assembly according to claim 5, wherein the volume of air has a relative humidity ranging from about 10% to about 50%.

9. The capsule pressure control assembly according to claim 1, wherein the volume of air cools the at least one capsule for at least 3 minutes.

10. The assembly according to claim 1 comprising a heating element for heating a quantity of fill material for filling capsules to an elevated temperature and an encapsulator for metering the heated fill material into capsules to form heated capsules.

11. The capsule pressure control assembly according to claim 10 wherein the cooling device is operable to reduce increased pressure caused by entrapped air in the heated capsule, to impede expansion of the capsules beyond a predetermined limit.

12. The assembly of claim 1 wherein the support unit comprises a movable transport for conveying heated capsules and the cooling device comprises one or more fans for providing forced air convection for the heated capsules, wherein the movable transport comprises a plurality of opening for allowing the convective flow through the transport.

13. The assembly of claim 12 wherein the fans are configured to provide a down draft flow over the heated capsules and through the transport.

14. The assembly of claim 12 wherein the movable transport comprises a conveyor having:
  a width;
  a length extending from an input at which heated capsules are loaded onto the conveyor and an output at which the capsules are discharged from the conveyor;
  a top surface; and
  a plurality of partitions projecting upwardly from the top surface of the conveyor, wherein the partitions have edges adjacent to or engaging the sidewalls.

15. The assembly of claim 14 wherein the cooling device comprises a plurality of movable receptacles for receiving heated capsules and conveying the heated capsules over the one or more fans, wherein each receptacle comprises:
  a front wall formed by a first one of the partitions;
  a rear wall formed by a second one of the partitions; and
  sides formed by the sidewalls;
  wherein the receptacles are formed so that front and rear walls form intersections at which any spacing between the front and rear walls and the sides is less than the smallest dimension of the capsules.

16. A capsule pressure control assembly for lowering the internal pressure of a capsule, the capsule pressure control assembly comprising:
  a capsule receiving assembly configured to cooperate with the discharge of an encapsulating machine to receive capsule containing medicine in a melted polymeric matrix at a temperature substantially higher than ambient temperature for the assembly, wherein the capsule receiving assembly comprises a plurality of movable receptacles for receiving heated capsules and conveying the heated capsules toward a cooling assembly, wherein each receptacle comprises a fluid permeable floor and:
    a front wall formed by a first partition;
    a rear wall formed by a second partition; and
    sidewalls;
    wherein the receptacles are formed so that front and rear walls form intersections at which any spacing between the front and rear walls and the sides is less than the smallest dimension of the capsules; and
  wherein the cooling assembly is adjacent the capsule receiving assembly and is operable to drive a flow of fluid through the permeable floor to impede expansion of air in the matrix in the capsules following discharge of the capsules from the encapsulating machine.

17. The capsule pressure control assembly of claim 16 wherein the cooling assembly is operable to cool the capsules from the time the capsule are discharged from the encapsulator until any air in the polymeric matrix material cooled sufficiently to substantially eliminate the likelihood of capsule elongation due to expansion of the air within the capsules.

18. The capsule pressure control assembly according to claim 16, wherein the cooling device is a fan where a volume of air is drawn past at least one filled capsule.

19. The capsule pressure control assembly according to claim 18, wherein the volume of air has a temperature ranging from about 10° C. to about 60° C.

20. The capsule pressure control assembly according to claim 18, wherein the volume of air has a relative humidity ranging from about 10% to about 50%.

* * * * *